United States Patent [19]

Rosen et al.

[11] Patent Number: 4,632,116
[45] Date of Patent: Dec. 30, 1986

[54] MICROELECTRONIC AXON PROCESSOR

[76] Inventors: Joseph M. Rosen, #49 Peter Coutts Cir., Stanford, Calif. 94305; Morton Grosser, 1016 Lemon St., Menlo Park, Calif. 94025

[21] Appl. No.: 826,940

[22] Filed: Feb. 6, 1986

Related U.S. Application Data

[63] Continuation-in-part of Ser. No. 626,187, Jun. 29, 1984, abandoned.

[51] Int. Cl.[4] .............................................. A61B 19/00
[52] U.S. Cl. ................................................ 128/419 R
[58] Field of Search ........... 128/334 R, 334 C, 419 R; 3/1.1

[56] References Cited

U.S. PATENT DOCUMENTS

| | | | |
|---|---|---|---|
| 3,916,905 | 11/1975 | Kuhn ............................... | 128/334 R |
| 4,026,300 | 5/1977 | DeLuca et al. ........................... | 3/1.1 |
| 4,306,561 | 12/1981 | De Medinaceli ............... | 128/334 C |

OTHER PUBLICATIONS

D. L. Jewett et al, *Nerve Repair and Regeneration Its Clinical and Experimental Basis*, ©1980, The C. V. Mosby Company, St. Louis, Toronto, London, pp. 105-114.

G. E. Loeb et al, "Analysis and Microelectronic Design of Tubular Electrode Arrays Intended for Chronic Multiple Single Unit Recording From Captured Nerve Fibers", *Med & Biol Eng & Comput*, Mar. 1977, vol. 15, pp. 195-201.

Mannard, "Regeneration Electrode Units: Implants for Recording from Single Peripheral Nerve Fibers in Freely Moving Animals", *Science*, Feb. 1974, vol. 18, pp. 547-549.

R. Llings et al, M. L. Phillips, Editor, "Implantable Monolithic Wafer Recording Electrodes for Neurophysiology", *Brain Unit Activity During Behavior*, ©1973, Charles C. Thomas Springfield, Ill., pp. 105-111.

*Primary Examiner*—William E. Kamm
*Assistant Examiner*—Mitchell J. Shein
*Attorney, Agent, or Firm*—Townsend and Townsend

[57] ABSTRACT

Normal nerve function is restored across severed ends of a nerve fascicle by inserting between the severed ends a laminated chip perforated with an array of holes each sized to accommodate approximately one axon and each containing at least two electrically conductive regions in ohmic contact with the inner surface of the hole at discrete locations along the axial direction of the hole. Proximal axon segments are permitted to propagate through the holes to join distal segments in random fashion and to be in contact with each of the two electrical contacts. Each contact is part of a circuit pattern capable of monitoring impulses, applying blocking potentials and placing selected pairs of proximal and distal axon segments in electrical contact such that nerve impulses can be routed as desired to restore normal nerve impulse communication and hence nerve function.

3 Claims, 4 Drawing Figures

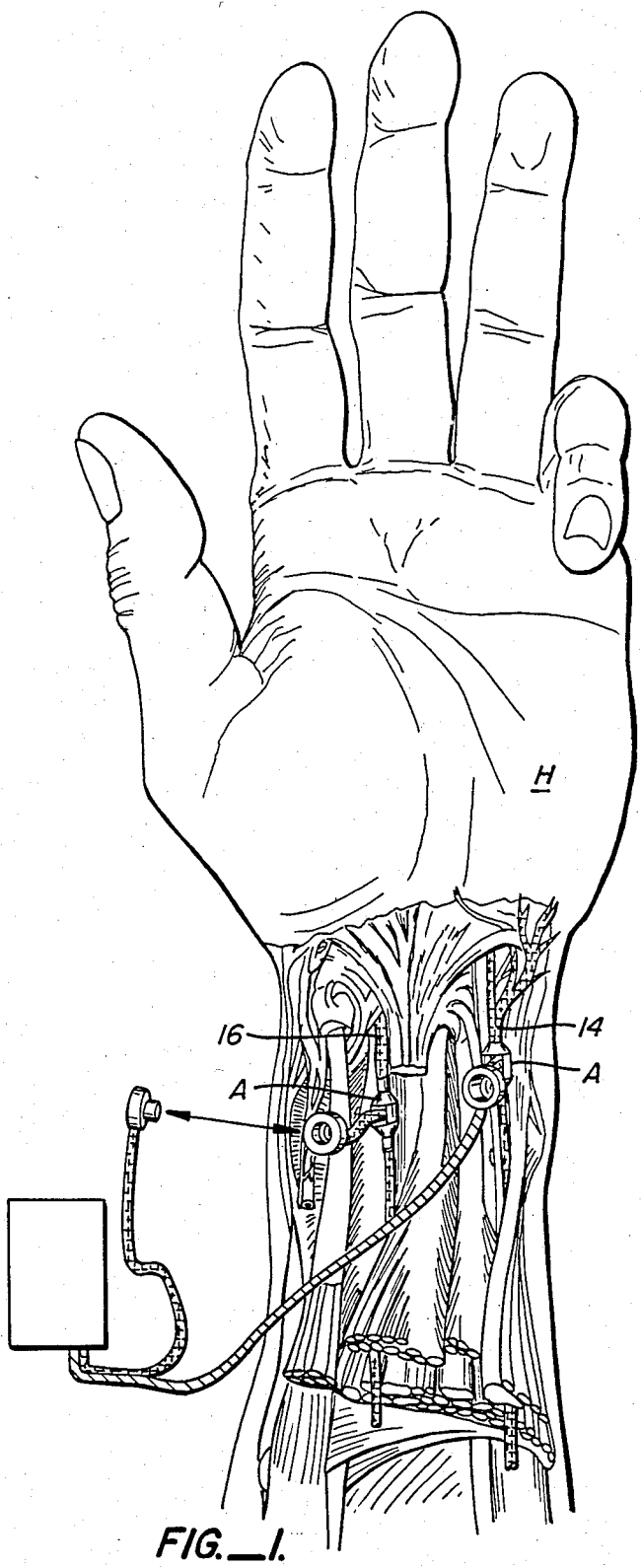
FIG._1.

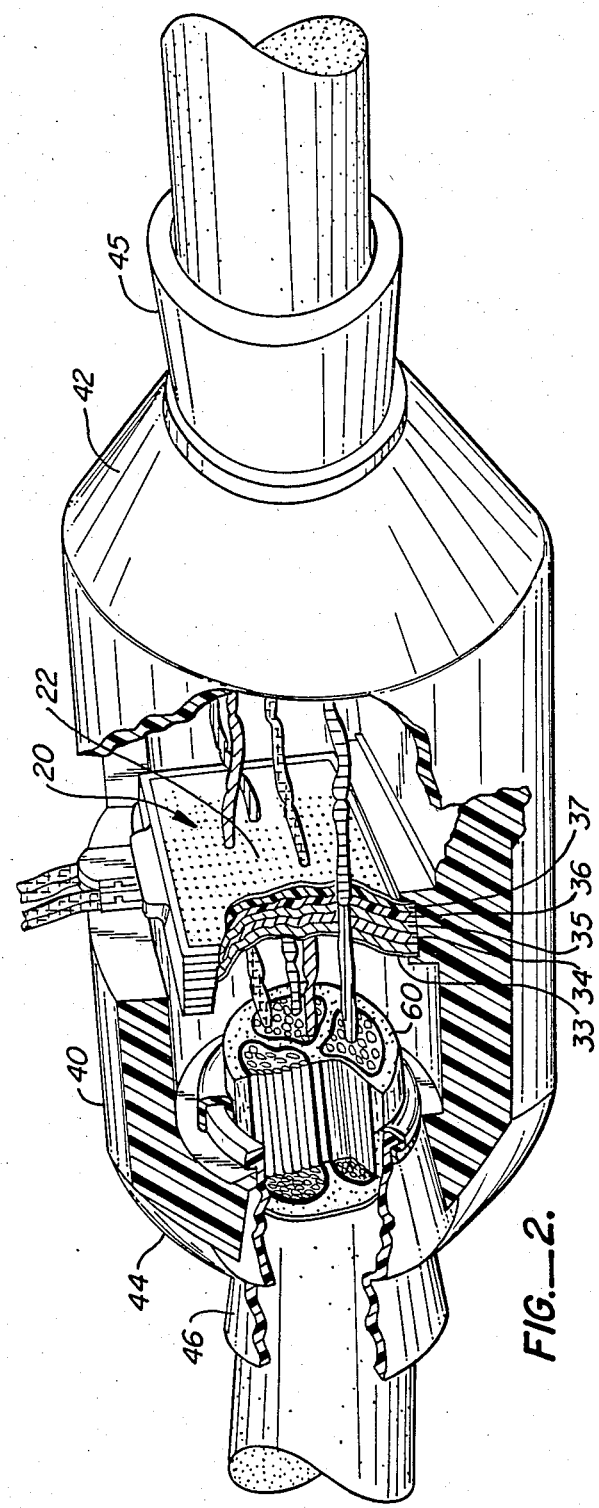
FIG._2.
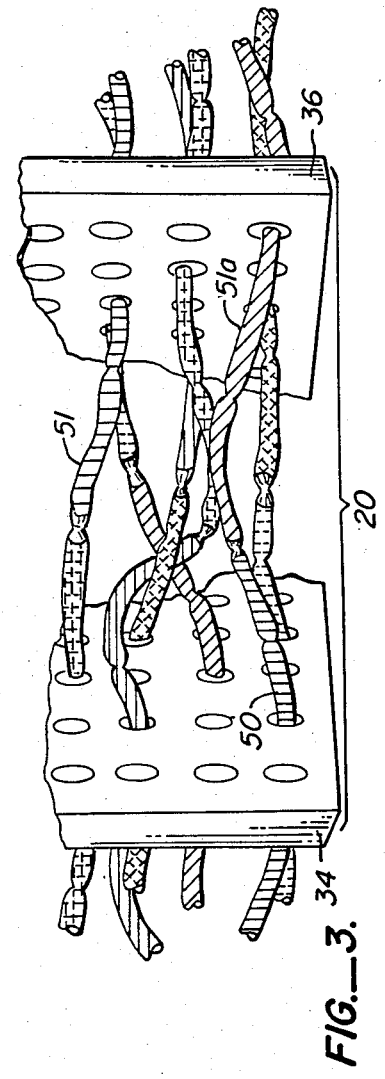
FIG._3.

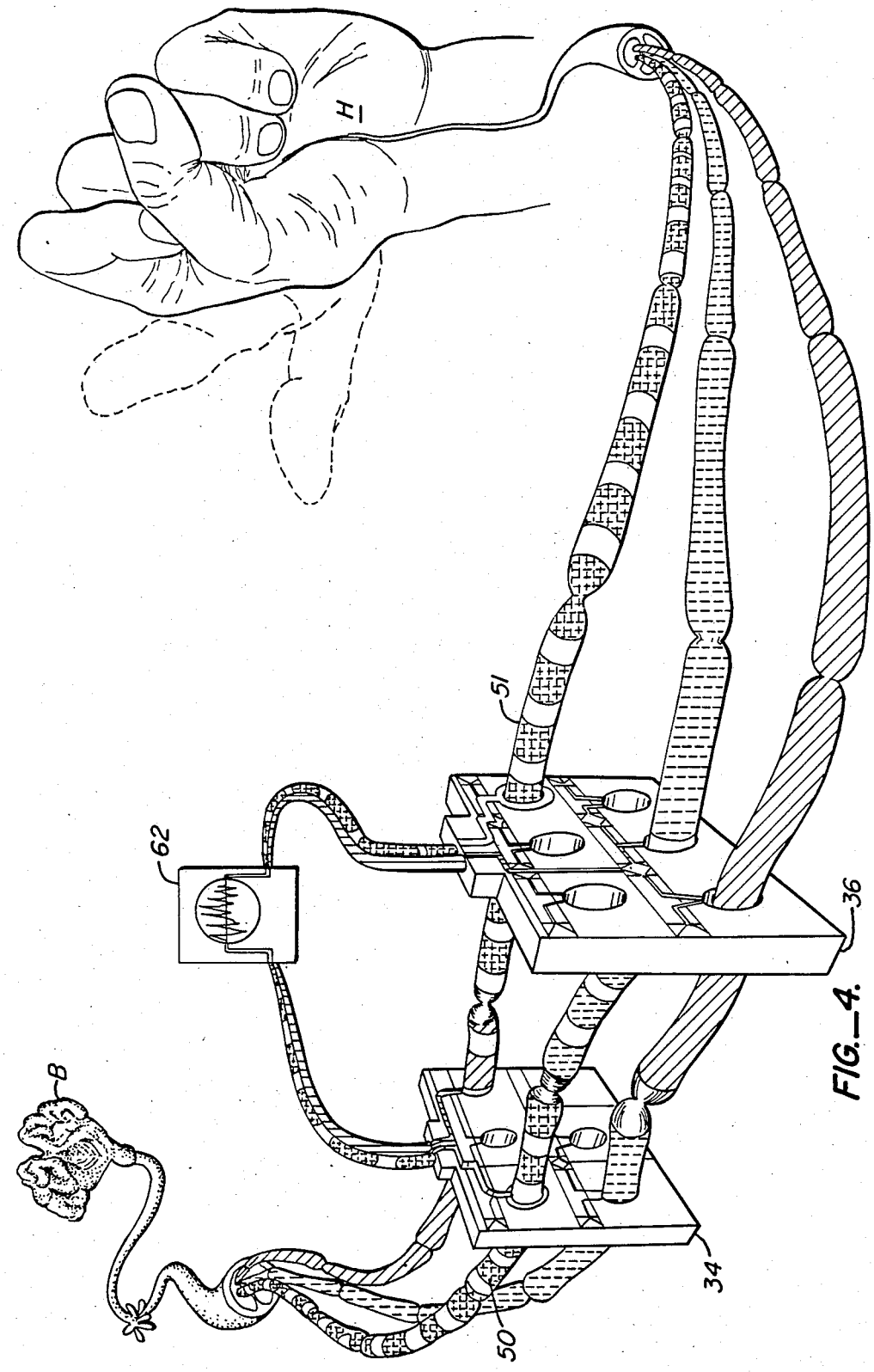
FIG._4.

MICROELECTRONIC AXON PROCESSOR

This application is a Continuation in Part of Ser. No. 626,187 filed June 29, 1984 now abandoned.

BACKGROUND OF THE INVENTION

A human or higher animal peripheral nerve consists of an elongated bundle of fibers resembling an electrical cable. The nerve has an outer jacket, the epineurium, and is internally divided into sub-cables called fascicles. One nerve can include many fascicles, each one sheathed in a perineurium. The fascicles are made up of groups of nerve fibers, each fiber comprising a sheath of Schwann cells and a conductive process called the axon. A typical axon measures 20 microns or less in diameter, so that a nerve 1 mm in diameter may have 2000 axons. Each axon can transmit discrete electrical impulses like an individual insulated wire in a cable.

Nerves are defined as radiating from the brain or central nervous system—proximal—to a limb or end organ—distal. Nerve impulses are transmitted along the axons in both directions. These neural impulses, or axon depolarizations, function like the signals in a digital electronic network; they are detected as being either on or off. In the nervous system, as in a digital circuit, it is the number and frequency of the impulses, rather than their individual differences, that determine the system behavior. Human nerve impulses have a depolarization voltage of about 100 millivolts and a current density of 4-10 picoamperes per square centimeter.

The electrical signals in the nervous system are both excitatory and inhibitory. That is, depending on their source and destination, they may stimulate an action or prevent it from occurring. Both kinds of signals are transmitted through the system simultaneously. Such nerve impulses have been detected and recorded from individual axons for many years.

When a nerve is severed surgically or by accidental trauma, neural impulses cannot cross the gap. It is possible to reconnect severed nerves by microsurgical techniques. The outer sheath will heal in a few weeks, and the axons will regenerate from the proximal to the distal direction in a somewhat longer time. Electrical function will be restored in six to nine months. However, it has been shown repeatedly that even though a repaired nerve looks complete both externally and in section, the end organs served by it seldom regain more than a fraction of their original function, except in young children.

One reason for this is scale. Although the suturing of a 1 mm-diameter nerve looks to an untrained eye like fine work, it is extremely coarse compared to the structure of the nerve. To make a perfect nerve repair, one would have to connect each one of thousands of severed axons to its correct path on the opposite side of the break, a task beyond the present state of neurosurgery. In fact, following a nerve lesion the proximal axons become compartmented in many new and smaller fascicles and propagate distally in random fashion, so there is no guarantee that any of the original neural paths will be re-established. It is easily possible that a proximal axon carrying an excitatory impulse may connect to a distal path which originally received an inhibitory signal.

However, because of the organization of the nervous system, it is sometimes possible to restore partial function with a less-than-perfect repair. The system is highly redundant—that is, the same information may be transmitted simultaneously over a number of axons, any one of which is capable of activating the end organ. In many cases where a nerve was almost, but not completely severed, a high percentage of original end organ function was retained despite the greatly reduced signal path. This indicates that loss of function after repair of a completely severed nerve is due not only to the interruption of actuating impulses, but also to inhibitory mismatching when the nerve is reconnected.

The regeneration of severed axons from the proximal face is irresistible. It is led by branching probes from the Schwann cells in the axon sheath. If the two severed ends of a nerve are brought into close terminal alignment, the proximal axons will propagate through the first axon tubule they reach on the distal side of the break—not necessarily, or even probably, the correct one. The large number of mismatched axon connections after a nerve repair almost guarantees that end organ function will be seriously limited. Our invention is an attempt to correct that situation.

SUMMARY OF THE INVENTION

It has now been discovered that severed nerve ends can be rejoined to restore normal nerve function by the use of a chip perforated with an array of holes, each sized to accommodate approximately one axon and containing two electrical contacts spaced apart axially. The chip is inserted between the severed fascicle ends so that the proximal axons will propagate through the holes, approximately one per hole, prior to joining to distal axons in random manner. Through impulse monitoring, applying blocking potentials and placing selected pairs of proximal and distal contacts in electrical connection, nerve impulses from axons in the proximal end are routed to distal axons such that normal impulse communication and nerve function is substantially restored.

BRIEF DESCRIPTION OF THE DRAWINGS

FIG. 1 is a picture of a hand in physiological section illustrating the ulnar nerve and the median nerve with the apparatus of this invention installed thereto;

FIG. 2 is a section of one of the chips of FIG. 1 illustrating the chip of this invention with axon regeneration partially shown from the proximal to the distal direction. Note that the regeneration does not communicate the axons correctly.

FIG. 3 is a schematic of FIG. 2 with the chip broken in half illustrating the incorrect axon communication;

FIG. 4 is a diagram showing the median nerve controlling the thumb of a human hand with the chip schematically shown as in FIG. 3 effecting the correct axon connection.

DETAILED DESCRIPTION OF THE INVENTION

Referring to FIG. 1, a hand H is illustrated with the ulnar nerve 14 and the median nerve 16 each having a microelectronic axon processor A attached thereto. A typical processor A is shown in more detail in FIG. 2.

Referring to FIG. 2, in the central portion of the processor between two severed and confronted nerve ends is a chip 20.

The chip 20 of the present invention is any insulating or semiconducting thin planar wafer. Examples of suitable materials are sapphire and silicon. The chip may be of any size that is capable of being inserted transversely between the ends of a severed nerve. The appropriate size will depend on the organism in which the device is implanted as well as the size of the nerve. For human usage, a typical size is 1mm square with a thickness of about 50 to 100 microns. This is illustrated in FIG. 2.

The chip is perforated with a grid or array of through holes 22, each sized to accommodate approximately one axon. A typical size is approximately 3 microns in diameter. The holes may be drilled or through-etched by various techniques, such as, for example, by the use of a YAG laser. Although the holes may be of any number or arrangement, devices for human usage will generally contain from about 1000 to about 2500 holes in a two-dimensional array, such as for example a rectangular or staggered grid.

The contacts are formed by electrically conductive traces in ohmic contact with discrete regions on the inner wall of the hole fabricated by conventional microelectronic techniques. There are at least two such regions per hole at different locations along the hole axis. This is conveniently achieved in the embodiment of FIG. 2 by using a laminated chip containing two parallel layers of conductive traces 34, 35 separated by a layer 35 of nonconductive material. The chip is preferably further encased in nonconductive material in the form of outer layers 33, 37 at each face of the chip, for protective purposes and the avoidance of undesired bridging or short circuiting between the traces.

The contacts are part of a circuit pattern connecting the inner hole surfaces to electrical components either on the periphery of the chip, entirely external to the chip, or within the conductive trace layers themselves. Such components may include monitoring devices, a power source, transmission gates, amplifiers and the like. The circuit will also connect pairs of proximal and distal contacts according to a pattern to be determined once the impulses and functions are properly matched. The circuitry may be located both in the regions of the chip surrounding the holes and on the chip periphery, and will generally consist of paths made of any conductive material, such as gold, silver, or copper. They may be singular, separate circuits for parallel access to a number of individual holes simultaneously, or they may incorporate any combination of serial or shared paths for sequential, phased, or multiplexed access.

A given contact will be constructed by conventional microelectronic techniques. A contact may completely surround a hole at a particular location along the axis, or there may be two or more contacts at the same axial location, for example a pair of contacts in the form of semicircular arcs separated by an insulating gap and each provided with a separate conductive path to the edge of the chip. The contact points on the periphery of the chip are accessible from either conductive trace layer for the attachment of external leads, either parallel, serial, or combinations thereof as desired.

The external leads may be made of any insulated conductive materials such as gold or silver, and they may be attached to the chip by mechanical, electrochemical, or thermal processes such as wedge-bonding, welding, or soldering. The entire chip and lead assembly can be treated, passivated, and/or imbedded in a protective material or housing, so as to insure its tolerance by the in vivo biological environment and its operation therein.

To use the present invention for nerve repair, the sterilized chip is inserted transversely between the ends of a severed nerve. Auxiliary devices such as mounting tubes, frames, clips, suture anchors, slotted tubules, or similar structures may be used to stabilize the chip with its faces parallel to the severed ends of the nerve, and to maintain the chip in contact with or close to the nerve ends. As the nerve heals, axons regenerating from the proximal face of the chip will grow through the holes and propagate into distal axon tubes.

Referring to FIG. 2, the chip 20 is shown encased in a cylindrical casing 40 constructed from polyglycolic acid (commonly known as PGA). The tube includes two frustoconical ends 42, 44 with protruding and conically flared nerve receiving portions 45, 46.

The severed nerve 60 is shown proximally confronted to the chip 20 with axon regeneration extending to and toward the distal portion of the nerve (hidden).

The axon connections thus established will still be random as when the nerve regenerates after suturing or reconnection by other means. However, by virtue of the electrical contacts at the inner surfaces of the holes, the axons extending through each hole are electrically accessible on an individual basis from either side of the chip, i.e., from either of the two conductive trace layers. This means that the nerve impulses in individual axons can be identified and recorded from the proximal contacts as they have been from single point electrodes for many years. It also means that axon paths established between the chip face (i.e., the distal contacts) and end organs can be traced and identified, again by using existing techniques of stimulation and recording. The same can be done on the proximal side for correlating specific axons with specific brain impulses.

Once the functions of the individual proximal and distal segments of the rejoined axons have been identified, the segments can be rerouted such that proximal and distal segments which correspond in end function can be placed in electrical contact, thus providing direct pathways for the nerve impulses (i.e. stimulating potentials). This is achieved by first recording the nerve impulses of all axons passing through the device, then identifying the end organ of any distal axon, and finally matching up correct paths via external shunts between the two planar contact layers, thereby restoring correct end organ function. In preferred embodiments, multiple contacts at each level permit the application of a blocking potential to any through axon on either side of the chip to prevent a shunted nerve impulse from short-circuiting or propagating into the wrong channel.

Referring to FIG. 3, an exploded version of the chip 20 is illustrated. For ease of understanding, the chip has been broken into two segments with only the conductive layers 34 and 36 being shown.

Axon regeneration is illustrated. It can be seen by the coding on the respective axons that proximal axon 50 should have joined at distal axon 51. However, junction has occurred to an axon 51a, making an improper connection. Loss of use of that motor and/or sensory segment of the body that is serviced by the axon will occur.

Referring to FIG. 4, the process for rerouting the nerve through the chip segments 34, 36 is illustrated.

It will be understood that the nerve will usually be severed by trauma. Upon initial repair, the nerve will be placed within the cylindrical casing 40 and confronted to the chip 20. An attempt will be made to register the respective fascicles on both sides of the chip into correct confronting relationship. This may be done by using visible clues on the exterior of the epineurium. The limb will typically be immobilized for a period of two weeks.

Before rerouting of the axons can take place, a sufficient interval of time must be allowed to elapse to permit the completion of proximal to distal regeneration. This will be in the order of six months. The axons will actually propagate through the holes in the chip 22. Once this regeneration has taken place, rerouting of the axon signal can occur. Using the radial nerve which controls motor impulses of the thumb as an example, the rerouting can be readily understood.

Specifically, and at the proximal nerve axon 50, ohmic contact is made and routed through a control network 62. Typically at network 62, a nerve impulse from the brain B is recorded. This signal is then randomly played to the axons transpiercing conductive portion 36. When the signal is played to the median nerve at axon 51, motor function will occur. This motor function will cause the thumb to move.

Thereafter, ohmic contact is maintained between the aperture of axon 50 and the aperture of axon 51. Axon 50 is blocked distally at layer 36, axon 51 is blocked proximally at layer 34. There results a restoration of normal motor control.

A further application of the chip disclosed herein is in improving the function of an ailing or deficient nervous system. Many neurological researchers have been able to trigger end organs with externally synthesized nerve impulses which are injected into the nervous system through point electrodes of various materials. The chip of the present invention when combined with appropriate circuitry may be used as a multiple switchboard and injection grid for externally generated signals to trigger an end organ or inhibit an undesirable nerve transmission such as "phantom pain." It may also be used as a monitoring interface for receiving signals from distal sensors and stimulating the appropriate proximal pathways to the brain. Means for achieving these effects will be readily apparent to those skilled in the art. For example, blocking may be achieved by lowering the potential at one of the contacts for a given axon (hyperpolarization) to a level sufficiently far below the threshold level for an action potential in that axon, such that all normal nerve impulses propagating from the region surrounding that contact will remain below the threshold. Alternately or in conjunction with the blocking potential, externally or artifically generated impulses can be transmitted to either the motor side or the sensory side by supplying then to the appropriate contact. On the other hand, boosting or amplification can be achieved by raising the axon potential (depolarization) or increasing the number of impulses to a given end function through the same fascicle (e.g., through axons of similar function). Further functions and means of manipulating the impulses passing through the axons will be readily apparent to those skilled in the art.

Any conventional power source may be used as a means for altering the potential or boosting pulse amplitudes. The power source may be either external or embedded in the patient in close proximity to the implanted chip. A rechargeable cell under the skin is a notable example.

In addition to the application described above, the device of the present invention may be used for an even broader range of utility by incorporating other electronic functions in the chip using semiconductor fabrication techniques. For example, the chip can include integral detectors, amplifiers, multiplexers, bridges, and similar electronic devices. A notable example is the use of a MOSFET gate transistor as part of the chip itself.

In addition, circuits of appropriate size can be applied to the chip itself according to known techniques. A notable example is fusible link technology, wherein electrical connections are fixed on the chip or around the periphery of the axon-hole array after the chip has been secured in place and all impulses have been recorded and axon functions identified. Thus, nerve impulses can be blocked, boosted, overridden, altered, and replaced as well as rerouted, so as to improve nervous system function, and ultimately the patient, in a wide variety of ways.

The present invention thus provides an implantable electronic device that provides direct access to specific neural pathways in the human nervous system. It can be wired with a permanent program and encapsulated, or remain accessible from outside the body for continuous programming. It may be used to intercept, measure, redirect, suppress, enhance, alter, or provide sustitutes for neurological signals, thus providing a wide range of beneficial applications for therapeutic use.

The mammalian peripheral nervous system is composed of a wide range of axons from 0.2 micrometers in diameter to 20 micrometers in diameter. When these axons are cut the distal end undergoes (Wallerian) degeneration, and after a few days the proximal end sends out sprouts to reinnervate the empty distal pathways (Ramon y Cajal 1928 - Nobel Prize work). Whether the proximal axon is 20 micrometers in diameter or 1 micrometer in diameter, the initial sprouts are very small in size—of the order of 0.1 micrometers in diameter.

These sprouts have been observed to grow through 25 micrometer holes in a chip in the severed nerves of rats. After growing through the hole, they then increase in size.

If the holes are limited to 5 micrometers in diameter, only one or a few axons will be captured in each hole. The large axons that were 20 micrometers in size would now be limited in the maximum size to which they could regenerate within the chip, but they would still function at this smaller size, and connect biologically to end-organs distally.

A regenerating axon with a 20 micron proximal portion has a sub-micron distal end when it initially regenerates through the hole in the device. With time, maturation in the newly regenerated axon occurs and the axon diameter increases. The segment within the hole will not be able to grow in diameter beyond the size of the hole. The larger axons in the hole will probably, over time, exclude the smaller axons.

It is known that the average size of the distal axons in a regenerated nerve never returns to normal, but the axons do function, even though large proximal axons now have smaller distal ends. There is a large volume of literature to support this.

We will now address the question of a one axon-one hole requirement of an operational device.

It is true that the device requires a functional one-hole one axon arrangement. However, it should be noted that axons smaller than 2.1 microns in size will have an electrical signal that can be at or below noise level for detection and therefore cannot be electrically seen by the device. Therefore only axons larger than a predetermined size, say 2.1 microns, will be functional with respect to this device. If the holes were 5 microns in size, many holes would probably only have one axon per hole and would therefore be operational. It is noted, for an operational device, because of the large amount of overlapping and redundancy of the nervous system, not every axon needs to be captured.

However, even in the cases where there are more than one axon per hole, it is still possible to capture only one of the axons if the other axons are smaller than the predetermined size (2.1 micrometers) in diameter. Only one axon would be capturable at this size. The chip at such a hole and axon will be operational.

In the worst case, where more than one axon in a 5-micrometer hole was captured electrically, it is unlikely that there would be more than two or three axons larger than 2.1 micrometers within the same hole. It may be possible to differentiate between each of these axons by their signal phase, their characteristic wave shape or by other well-known electrophysiological techniques. Otherwise, such a hole may be ignored.

The foregoing description is offered by purposes of illustration. It will be readily apparent to those skilled in the art that modifications, variations, and alternative constructions and methods may be substituted for the various features described above, without departing from the spirit and scope of the invention, as defined by the appended claims.

What is claimed is:

1. Apparatus for restoring normal function to a severed nerve fascicle, comprising;
   a flat planar substrate perforated with a plurality of holes, each hole sized to accommodate one dominant axon;
   at least two electrically conductive traces in ohmic contact with the inner surface of each said hole at discrete locations along the axial direction of said hole, thereby defining a proximal contact and a distal contact;
   means for monitoring the potential at each said contact;
   means for individually applying a blocking potential to at least one contact in each hole; and
   means for communicating a stimulating potential between preselected pairs of proximal and distal contacts.

2. A process for restoring normal function to a severed nerve fascicle, comprising:
   (a) inserting between the severed ends of said fascicle a chip perforated with a plurality of holes, each hole sized to accommodate one dominant axon, said chip containing at least two electrical traces in ohmic contact with the inner surface of each said hole at discrete locations along the axial direction of said hole, said locations being designated a proximal contact and a distal contact, to permit the proximal axons of said severed ends to propagate through said holes and join with distal contacts;
   (b) detecting pulses at each said proximal contact in response to a command;
   (c) detecting function responses generated by applying electrical impulses to each said distal contact;
   (d) applying a blocking potential to selected axon segments through at least one of said contacts; and
   (e) electrically connecting each said proximal contact with a distal contact of corresponding function to restore normal nervous communication.

3. Apparatus for restoring normal function to a severed nerve fascicle comprising:
   a flat planar substrate perforated with a plurality of holes, each hole sized to accommodate one dominant axon;
   a sheath surrounding said flat planar substrate for confronting respective ends of severed nerves one to another at discrete axons;
   at least two electrically conductive traces in ohmic contact with the inner surface of each said hole at discrete locations along the axial direction of said hole, thereby defining a proximal contact and a distal contact;
   means for monitoring the potential at each said contact;
   means for individually applying a blocking potential to at least one contact in each hole; and
   means for communicating a potential between preselected pairs of proximal and distal contacts.

* * * * *